US009936915B2

(12) United States Patent
Emori et al.

(10) Patent No.: US 9,936,915 B2
(45) Date of Patent: Apr. 10, 2018

(54) SLEEP DISPLAY PROGRAM, SLEEP DISPLAY METHOD, AND SLEEP DISPLAY DEVICE

(71) Applicant: OMRON HEALTHCARE CO., LTD., Muko-shi, Kyoto (JP)

(72) Inventors: Yasuko Emori, Kyoto (JP); Yoko Kanemitsu, Kyoto (JP); Fumihiko Nakamura, Kyoto (JP); Feilang Tseng, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 0 days.

(21) Appl. No.: 14/367,556

(22) PCT Filed: Nov. 27, 2012

(86) PCT No.: PCT/JP2012/080604
§ 371 (c)(1),
(2) Date: Jun. 20, 2014

(87) PCT Pub. No.: WO2013/108488
PCT Pub. Date: Jul. 25, 2013

(65) Prior Publication Data
US 2014/0347366 A1 Nov. 27, 2014

(30) Foreign Application Priority Data

Jan. 20, 2012 (JP) .................. 2012-010513

(51) Int. Cl.
*G06T 11/00* (2006.01)
*A61B 5/00* (2006.01)
(52) U.S. Cl.
CPC ............ *A61B 5/4815* (2013.01); *A61B 5/742* (2013.01); *A61B 5/4812* (2013.01)

(58) Field of Classification Search
CPC .................. G06T 11/206; A61B 5/4815
(Continued)

(56) References Cited

U.S. PATENT DOCUMENTS 7,274,375 B1 * 9/2007 David ............... G06Q 10/06
345/619
8,629,887 B2 * 1/2014 Sasaki ............... B60K 35/00
345/440

(Continued)

FOREIGN PATENT DOCUMENTS

JP 2002-116271 A * 4/2002 .............. G04G 9/00
JP A-2002-116271 4/2002
(Continued)

OTHER PUBLICATIONS

International Search Report issued in International Application No. PCT/JP2012/080604 dated Jan. 22, 2013.
(Continued)

*Primary Examiner* — Devona Faulk
*Assistant Examiner* — Hai Tao Sun
(74) *Attorney, Agent, or Firm* — Oliff PLC

(57) ABSTRACT

Provided is a sleep display program, a sleep display method, and a sleep display device for visualizing an internal clock regarding sleep. The sleep display program is a program for displaying, in a display unit, sleep state data of a user that has been measured and recorded by a sleep evaluation device, the data including at least a wakeup time $T_W$ and a bedtime $T_Z$, and the program including a step of obtaining the data from the sleep evaluation device, a step of displaying, in the display unit, a 24-hour circular time display image divided into time periods that each indicate a predetermined span of time, and a step of plotting, on the time periods in (Continued)

the time display image, a set number of days' worth of records of the wakeup times $T_W$ and the bedtimes $T_Z$ included in the data.

9 Claims, 7 Drawing Sheets

(58) Field of Classification Search
USPC .......................................................... 345/440
See application file for complete search history.

(56) References Cited

U.S. PATENT DOCUMENTS

| 2008/0306351 | A1* | 12/2008 | Izumi ............................ 600/300 |
| 2009/0134819 | A1* | 5/2009 | Noguchi et al. .............. 315/308 |
| 2010/0049008 | A1* | 2/2010 | Doherty et al. ............. 600/301 |
| 2011/0015495 | A1* | 1/2011 | Dothie et al. ................ 600/300 |
| 2011/0151415 | A1* | 6/2011 | Darling ........................ 434/149 |
| 2011/0230790 | A1* | 9/2011 | Kozlov ................ A61B 5/4812 600/595 |
| 2012/0179061 | A1* | 7/2012 | Ramanan et al. ............ 600/538 |
| 2012/0287162 | A1* | 11/2012 | Aminian .............. G09B 29/007 345/660 |

FOREIGN PATENT DOCUMENTS

| JP | A-2003-216734 | 7/2003 |
| JP | A-2003-339674 | 12/2003 |
| JP | A-2006-61270 | 3/2006 |
| JP | A-2009-247386 | 10/2009 |
| JP | A-2010-148829 | 7/2010 |
| JP | 2011-050673 A | 3/2011 |
| JP | A-2012-187299 | 10/2012 |

OTHER PUBLICATIONS

Mar. 2, 2016 Office Action issued in Chinese Application No. 201280067618.9.

* cited by examiner

SLEEP DISPLAY PROGRAM, SLEEP DISPLAY METHOD, AND SLEEP DISPLAY DEVICE

TECHNICAL FIELD

The present invention relates to sleep display programs, sleep display methods, and sleep display devices for supporting an improvement in sleep rhythm.

BACKGROUND ART

Various conventional techniques have been disclosed with respect to devices for measuring sleep. For example, Patent Literature 1 (JP 2009-247386A) discloses a sleep determination device that determines a sleep state of a subject by placing a sensor on a bedding article such as a bed and comparing a determination threshold between heavy and light movement of the subject with a signal indicating body movement.

CITATION LIST

Patent Literature

Patent Literature 1: JP 2009-247386A

SUMMARY OF INVENTION

Technical Problem

However, sleep has a deep relationship with daily lifestyle habits, and thus simply measuring sleep does not provide a strong enough motivation to improve sleep habits such as when to go to sleep, when to wake up, and so on.

The first step in supporting an improvement in lifestyle habits is correctly identifying the current situation and cultivating an awareness of problem points. Nevertheless, the rhythm at which hormones are secreted is also said to influence human sleep rhythms, and thus visualizing the internal clock that controls sleep is considered to be extremely important. Furthermore, it is necessary to continue to provide motivation to improve sleep quality while also ensuring a correct foundation of knowledge.

Having been achieved in light of the aforementioned situation, it is an object of the present invention to provide a sleep display program, a sleep display method, and a sleep display device that visualize an internal clock related to sleep in order to support an improvement in sleep rhythm.

Solution to Problem

To achieve this aforementioned object, according to an aspect of the present invention, a sleep display program is a program for displaying, in a display unit, sleep state data of a user that has been measured and recorded by a sleep evaluation device, the data including at least a wakeup time $T_W$ and a bedtime $T_Z$, and the program including a step of obtaining the data from the sleep evaluation device, a step of displaying, in the display unit, a 24-hour circular time display image divided into time periods that each indicate a predetermined span of time, and a step of plotting, on the time periods in the time display image, a set number of days' worth of records of the wakeup times $T_W$ and the bedtimes $T_Z$ included in the data; here, the records are displayed visually in the time display image in association with an area, number, or color of a graphic or a combination thereof.

Preferably, the sleep display program further includes a step of inputting a subjective impression of the quality of the user's sleep after waking as a graded sleep evaluation index, and a step of visually displaying a result of the input in association with an area, number, or color of a graphic or a combination thereof.

Preferably, the sleep display program further includes a step of visually displaying a cumulative value of the sleep evaluation index from a point in the past to the present.

Preferably, the sleep display program further includes a step of displaying, in the time display image, a recommended bedtime period $T_{ZZ}$ set to a certain amount of time after a most recent planned wakeup time $T_S$.

Preferably, in the sleep display program, an end time of the recommended bedtime period does not exceed a pre-set time.

Preferably, the sleep display program further includes a step of displaying, in the time display image, a recommended wakeup time period $T_{ZW}$ calculated based on one of an average of planned wakeup times set in the past and the latest planned wakeup time that is currently set.

Another aspect of the present invention includes a case where the invention is realized as a mobile information terminal or another terminal apparatus having a screen display function in which the aforementioned program is installed. Yet another aspect of the present invention is a method for executing the steps of the aforementioned program.

BRIEF DESCRIPTION OF DRAWINGS

FIG. 4A is a block diagram illustrating a specific example of the hardware configuration of the sleep evaluation device 100, whereas

DESCRIPTION OF EMBODIMENTS

First Embodiment

Figure 1:
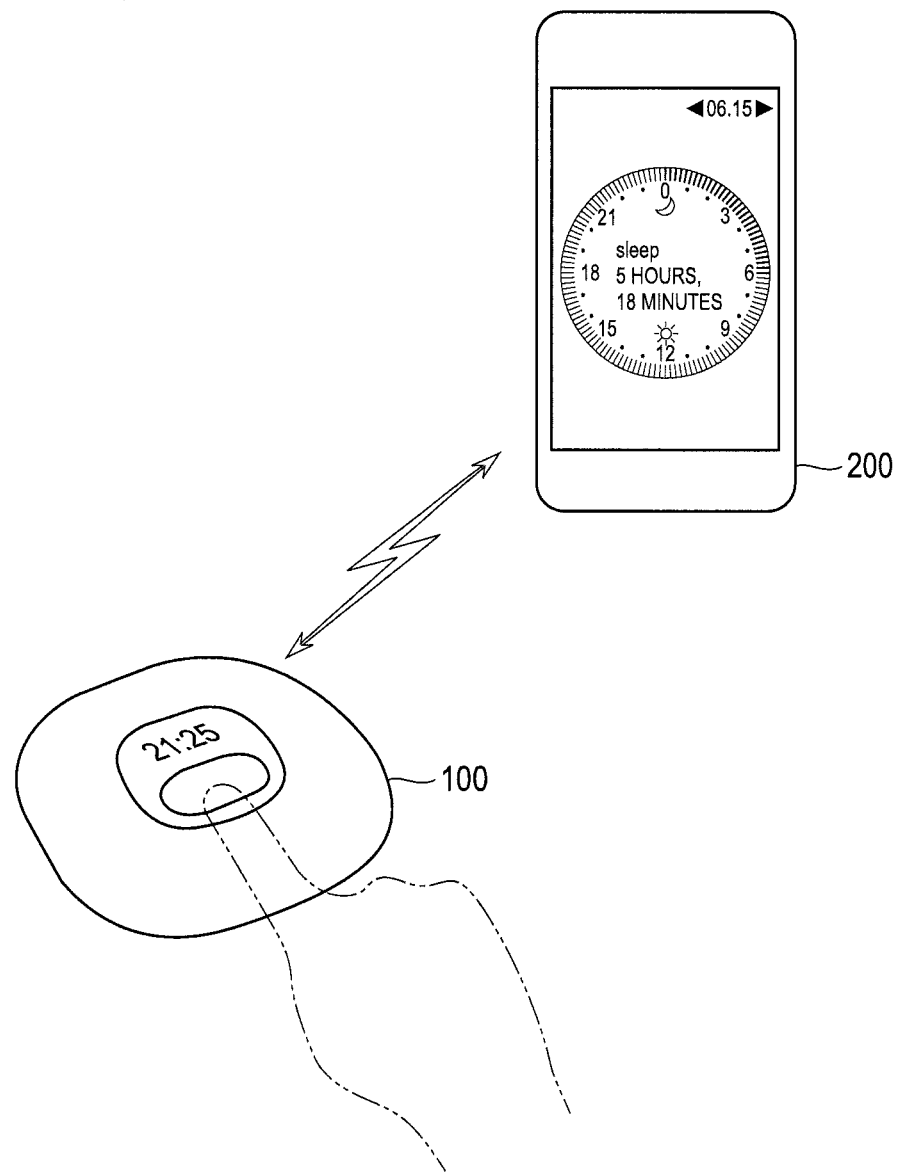
FIG. 1 is a diagram illustrating a specific example of the external appearance of a generic sleep evaluation device 100, as well as a sleep display device 200 in which a sleep display program according to an embodiment of the present invention has been installed.

Hereinafter, an embodiment of the present invention will be described with reference to the drawings. In the following descriptions, identical reference numerals are assigned to identical components and constituent elements. The names and functions thereof are also the same.

External Appearance

FIG. 1 is a diagram illustrating a specific example of the external appearance of a generic sleep evaluation device 100, as well as a sleep display device 200 in which a sleep display program according to an embodiment of the present invention has been installed.

Figure 4A:
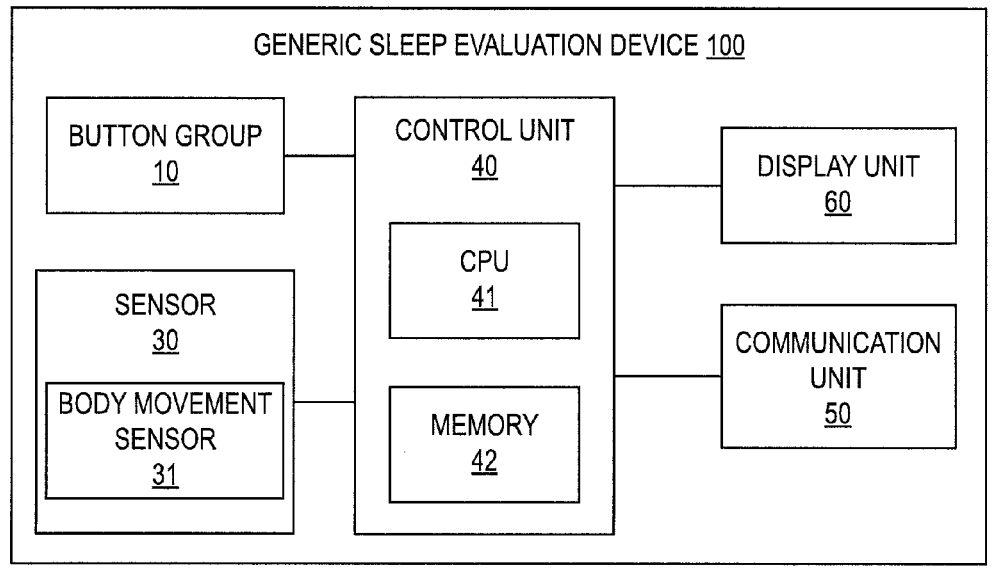

FIG. 4A is a block diagram illustrating a specific example of the hardware configuration of the sleep evaluation device 100.

A button group 10, a display unit 60, a sensor 30, and a communication unit 50 shown in FIG. 4A are all connected to a control unit 40. The sleep evaluation device 100 includes the communication unit 50 for communicating wirelessly or over wires. Using the communication unit 50, the sleep evaluation device 100 is connected to a sleep display device such as a personal computer ("PC" hereinafter), a mobile information terminal, or the like, and outputs "sleep state data", necessary for generating display data, to a display device 200.

The sleep evaluation device has a function for obtaining data used to determine the sleep state of a measurement subject (a user), the quality thereof, and so on, by employing, for example, an accelerometer, a Doppler sensor, an ultrasound sensor, by analyzing image data obtained by an image sensor, or by employing a combination of a plurality of such sensors. An alarm clock function for emitting an alarm at a planned wakeup time $T_S$ may also be provided. The alarm may emit a sound, music, may vibrate, or may perform a combination thereof. Any technique may be used as long as the technique realizes an alarm clock function for waking the user. The alarm clock function may further include a "snooze function" for temporarily stopping the alarm.

The control unit 40 includes a CPU (Central Processing Unit) 41 for performing overall control and a memory 42 for storing programs and the like executed by the CPU 41. The control unit 40 generates the sleep state data by the CPU 41 executing a display program stored in the memory 42 and executing computations using inputted operation signals and sensor signals.

Data outputted from the sleep evaluation device according to this embodiment includes at least the following information:
 the planned wakeup time $T_S$
 a wakeup time $T_W$
 a bedtime $T_Z$ Here, a time at which the alarm is set for is taken as the planned wakeup time $T_S$, a time at which the user wakes up is taken as the wakeup time $T_W$, and a time at which the user begins to sleep is taken as the bedtime $T_Z$. Note that although the sleep evaluation device is capable of detecting the time at which the user stops sleeping in addition to the time at which the user begins to sleep, it is thought that the user's intentions can be reflected by using the time at which the alarm is stopped as the wakeup time. For this reason, in the present embodiment, the time at which the user consciously stops the alarm clock function is taken as the wakeup time $T_W$, and the time at which the sleep evaluation device detects that the user begins to sleep is taken as the bedtime $T_Z$. The wakeup time may employ a result of measurement performed by the sleep evaluation device, or may employ the time at which the alarm is stopped or the like as described above. In the case where the snooze function has been used, it is preferable to output the time at which the alarm was last stopped. Various designs can be used in such a case. Furthermore, in the case where there are a plurality of wakeup times in the same day, it is reasonable to output the final time as the wakeup time.

The performance of a generic sleep evaluation device will vary greatly depending on the specifications thereof, but because the sleep display program described in the present embodiment is primarily intended to display information in a user's terminal, the reliability of the data and so on is not of paramount concern. The sleep evaluation device may therefore be a simplified device in which a body movement detection means is a simple means that uses a comparatively low-cost component such as an accelerometer or is designed as an algorithm. Even with such a device, accumulating data on a daily basis makes it possible to visually display average, maximum, and minimum values for sleep times, bedtimes, wakeup times, and so on in weekly or monthly units, for example, and an effect of supporting an improvement in the sleep rhythm can be anticipated as a result.

The communication unit 50 may communicate directly with the sleep display device 200 through wireless communication over, for example, infrared or Bluetooth (registered trademark) connections. Connecting the device with a terminal directly through a FeliCa port or the like and transferring data can be considered as such a direct connection. Various other communication methods can be considered, such as transferring data through wired communication over a USB cable connected to a USB terminal, transferring data using a memory card such as a USB memory, an SD memory, or the like as a medium, connecting through the TCP/IP protocol via an access point in a LAN and transferring data, and so on. Internet connection functionality may be provided and the communication unit 50 may communicate with the display device 200 over the Internet. In the case where the data transfer will occur over the Internet through a server, the data can be loaded into the sleep display device through the server. In this case, the data is uploaded via the Internet to the server, which has a function for storing the data. The necessary data is then downloaded to the client terminal via the Internet when a request from the client terminal has been received. If the sleep evaluation device is configured to periodically upload data to the server, the latest data can be obtained simply by using the terminal to synchronize the data with the server. The communication unit 50 is provided with the interfaces required to realize these communication functions.

Furthermore, the communication unit 50 may have a wireless LAN (Local Area Network) server function, and may send, to the display device 200 that has accessed the sleep evaluation device 100 over the wireless LAN, display data (mentioned later) written in a markup language such as HTML (Hyper Text Markup Language) or the like.

In addition to sending the sleep state data to the sleep evaluation device, the communication unit 50 may also have a function for configuring the alarm clock function and so on from the terminal side.

Figure 4B:
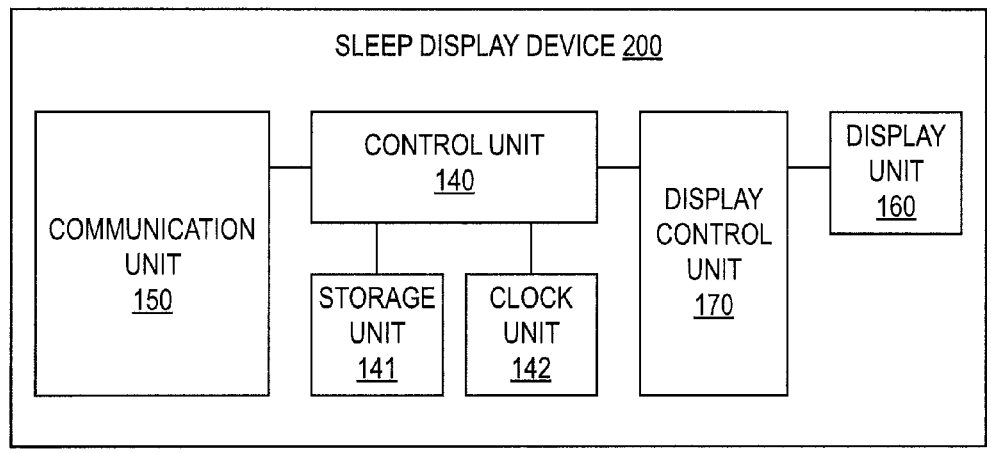
FIG. 4B is a block diagram illustrating a specific example of the hardware configuration of the sleep display device 200.

FIG. 4B is a block diagram illustrating a specific example of the hardware configuration of the sleep display device 200. The sleep display device 200 includes a control unit 140, a communication unit 150, a display unit 160, a display control unit 170, and so on. A storage unit 141, a clock unit 142, and so on are connected to the control unit 140. A generic device such as a mobile information terminal can be used as the sleep display device 200. The device need not be "mobile" per se, and may be a desktop, laptop, or tablet computer, as long as it is a terminal device having a display screen. This device will be referred to simply as a "terminal" hereinafter.

In other words, the terminal receives necessary "sleep state data" from the sleep evaluation device and displays that data so as to have a visual effect for the user, which in turn supports an improvement in the user's sleep rhythm.

Display Screen

Figure 2:
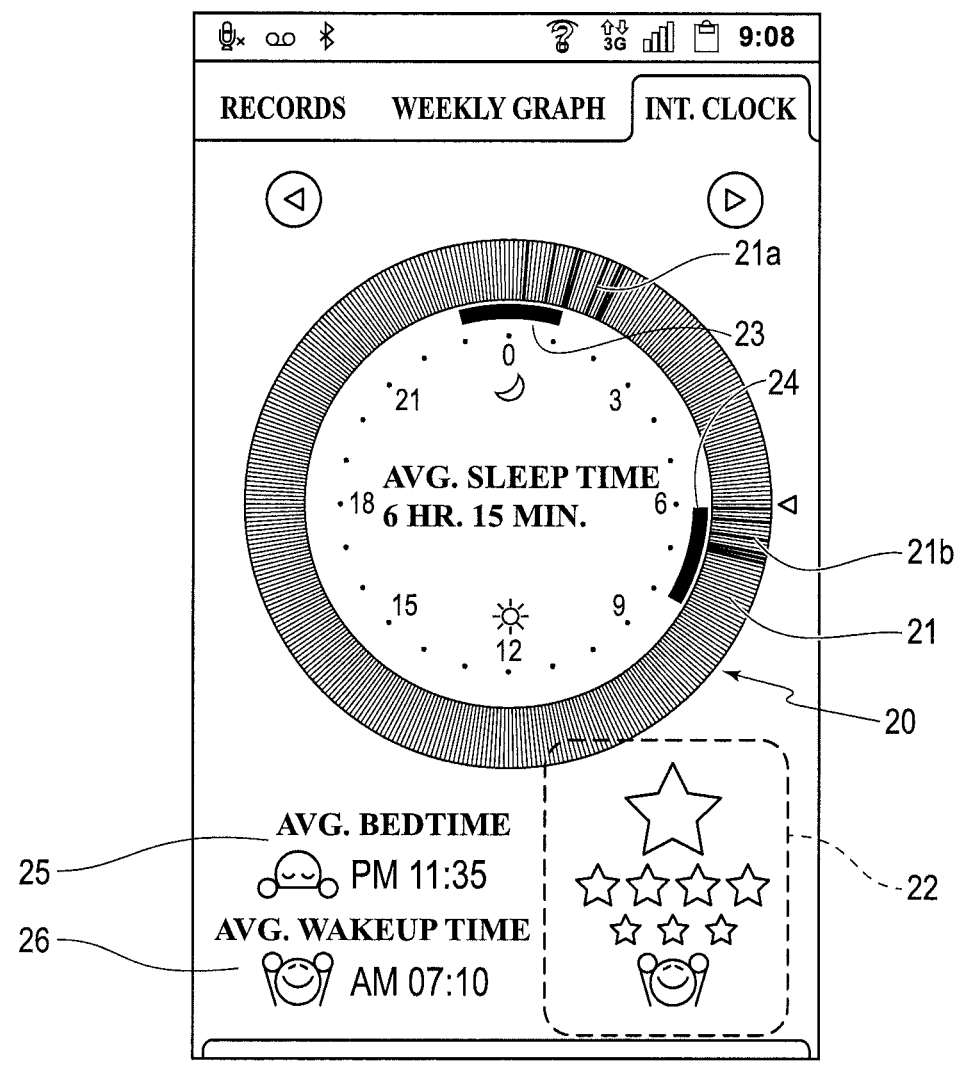
FIG. 2 is a diagram illustrating an example of a display screen in the sleep display device 200.

FIG. 2 is a diagram illustrating an example of a display screen in the sleep display device 200. A 24-hour circular time display image 20 is displayed prominently in the center, and time periods 21 are sectioned off thereon. As one example, the time periods 21 indicate time spans of 5-minute divisions resulting from dividing the 24 hours into 288 equal parts, and each time period indicates a record of the wakeup time or the bedtime. In this example of the time periods 21, three levels of brightness can be displayed in two colors, and the bedtime is displayed in blue (21a), whereas the wakeup time is displayed in red (21b). At a given time, the first instance of a record is plotted at 35% brightness, the second record is plotted at 70% brightness, and the third and subsequent records are plotted at 100% brightness. Plotting the records of past bedtimes and wakeup times while visually displaying those records in association with the area, number, color, or a combination thereof for a graphic in this manner can be expected to serve as a trigger for a user reevaluating his/her lifestyle habits.

Information aside from the wakeup time, the bedtime, and so on can also be displayed in the circular 24-hour time display image 20. For example, an "amount of time required to fall asleep", an "amount of time required to wake", and so on can also be displayed in response to user operations. The user providing information s/he personally feels is pertinent to his/her own sleep is useful in improving his/her sleep rhythm.

Figure 3:
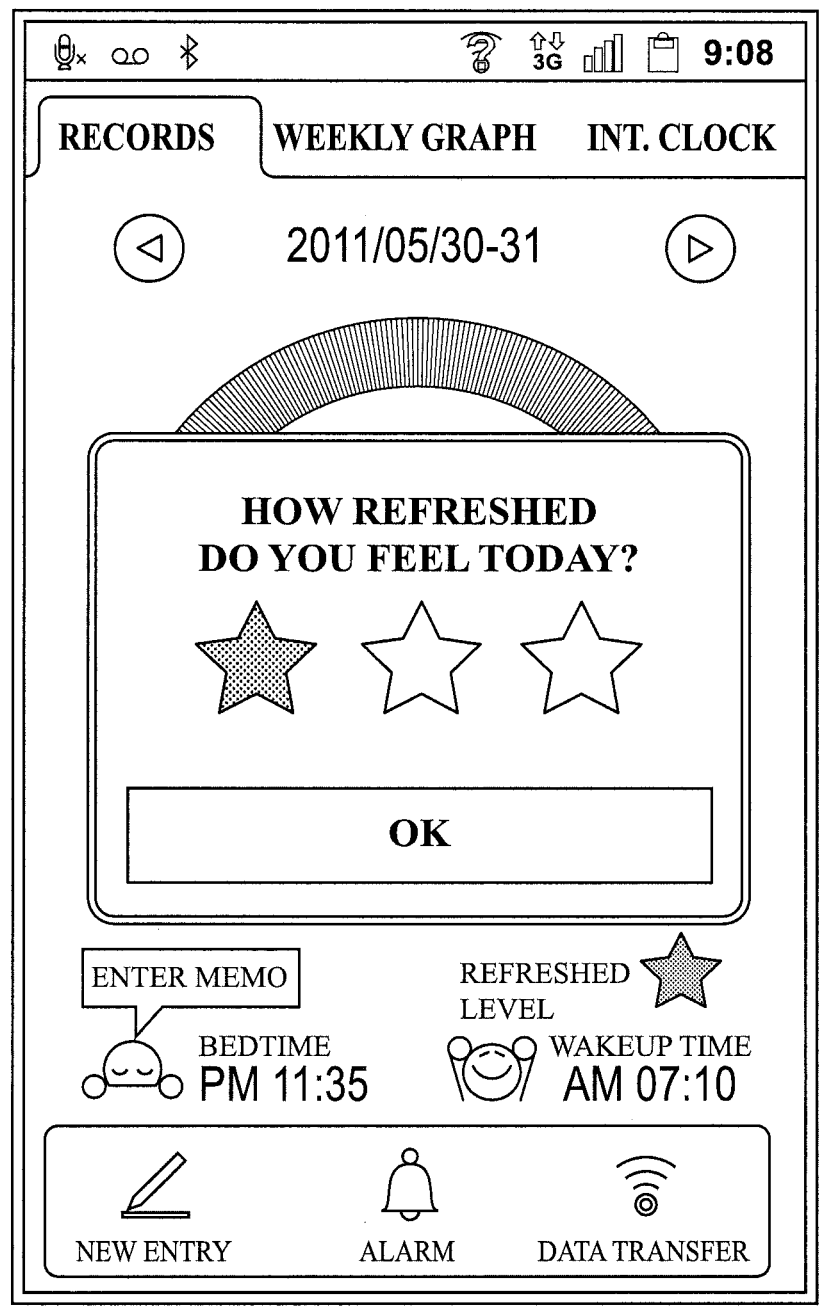
FIG. 3 is a diagram illustrating an input screen through which a user inputs a subjective impression of the quality of his/her sleep after waking as a graded sleep evaluation index.

FIG. 3 is a diagram illustrating an input screen through which a user inputs a subjective impression of the quality of his/her sleep after waking as a graded sleep evaluation index. In this example, the user is prompted to input this impression (a "refreshed level") as one of three grades.

Although it is possible to display only that day's "refreshed level" in the display screen of the terminal, it is more preferable to visually display the cumulative "refreshed level" from a point in the past up until the present, in a set period of weeks or months, for example. For example, the "refreshed level" inputted here is accumulated from the past and is displayed as the "refreshed level" in a display area 22 shown in FIG. 2, and is displayed based on the size (area) and number of stars. In this example, a single point is allotted for each star indicating the "refreshed level" inputted as indicated in FIG. 3, and a visual association is established by preparing a correspondence relationship in advance, where 10 normal stars result in a medium star and 50 medium stars result in a large star. Doing so builds a desire to increase the "refreshed level", which in turn serves as a motivator for improving the sleep rhythm.

Furthermore, it is preferable to display, in the time display image 20, a recommended bedtime period $T_{ZZ}$, set to a time occurring after a set amount of time has elapsed following the latest planned wakeup time $T_S$, as a "recommended bedtime zone" 23. Specifically, a time period between 16 and 18 hours following the planned wakeup time $T_S$, for example, is set to the "recommended bedtime period $T_{ZZ}$". In this case, it is preferable to set a condition that the time period does not exceed a pre-set time (for example, 1 AM).

Furthermore, it is preferable to display, in the time display image 20, a set amount of time after the planned wakeup time $T_S$ as a recommended wakeup time period $T_{ZW}$ (recommended wakeup zone) 24. In this example, a time period spanning from the planned wakeup time to two hours thereafter is set as the "recommended wakeup time period $T_{ZW}$".

An average bedtime 25, an average wakeup time 26, and so on may be displayed as necessary. The user may also be made able to edit past bedtimes, wakeup times, and so on after the fact.

As described thus far, displaying the records of bedtimes, wakeup times, and so on for each of set periods in the 24-hour circular time display image makes it possible to visually confirm variations therein. Also displaying the subjective evaluation serves as a motivator for increasing the "refreshed level" when waking up, which in turn prompts the user to improve his/her sleep rhythm.

Program Operations

Figure 5:
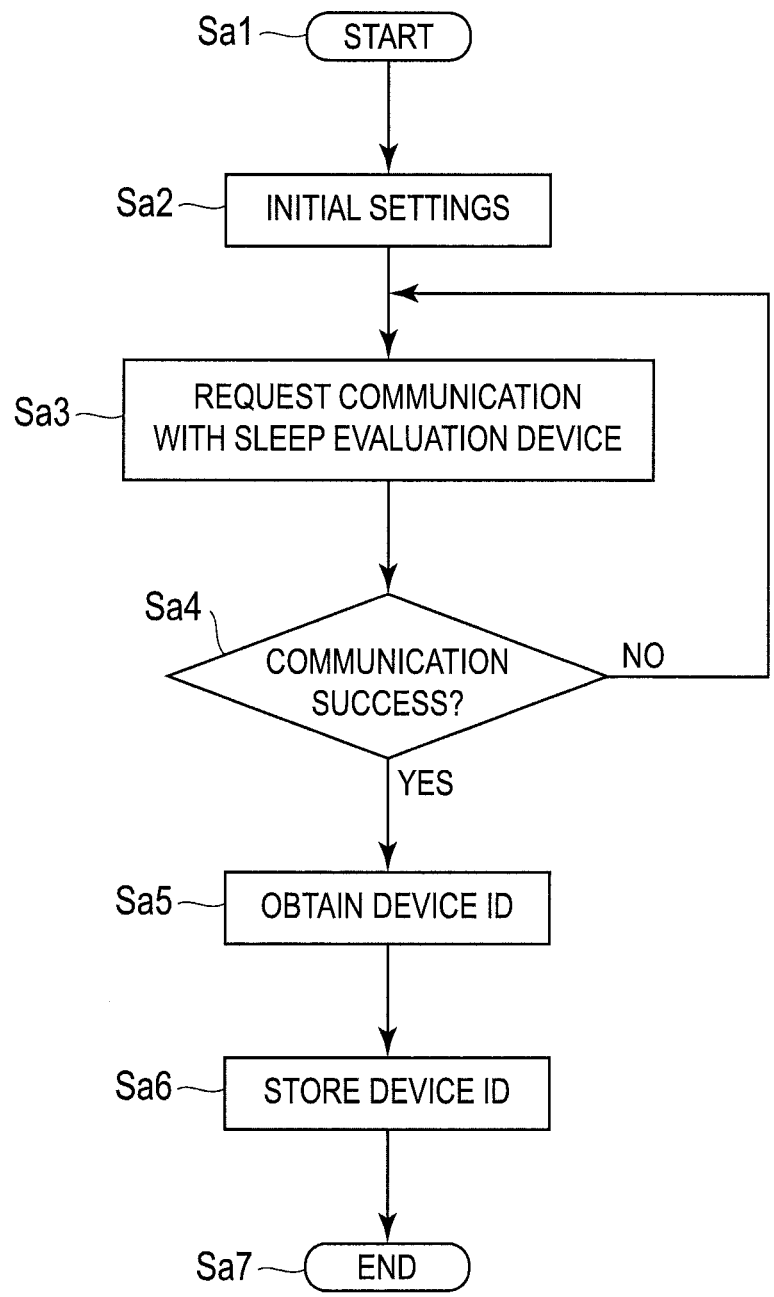
FIG. 5 is a flowchart illustrating basic operations of a sleep display program.
Figure 6:
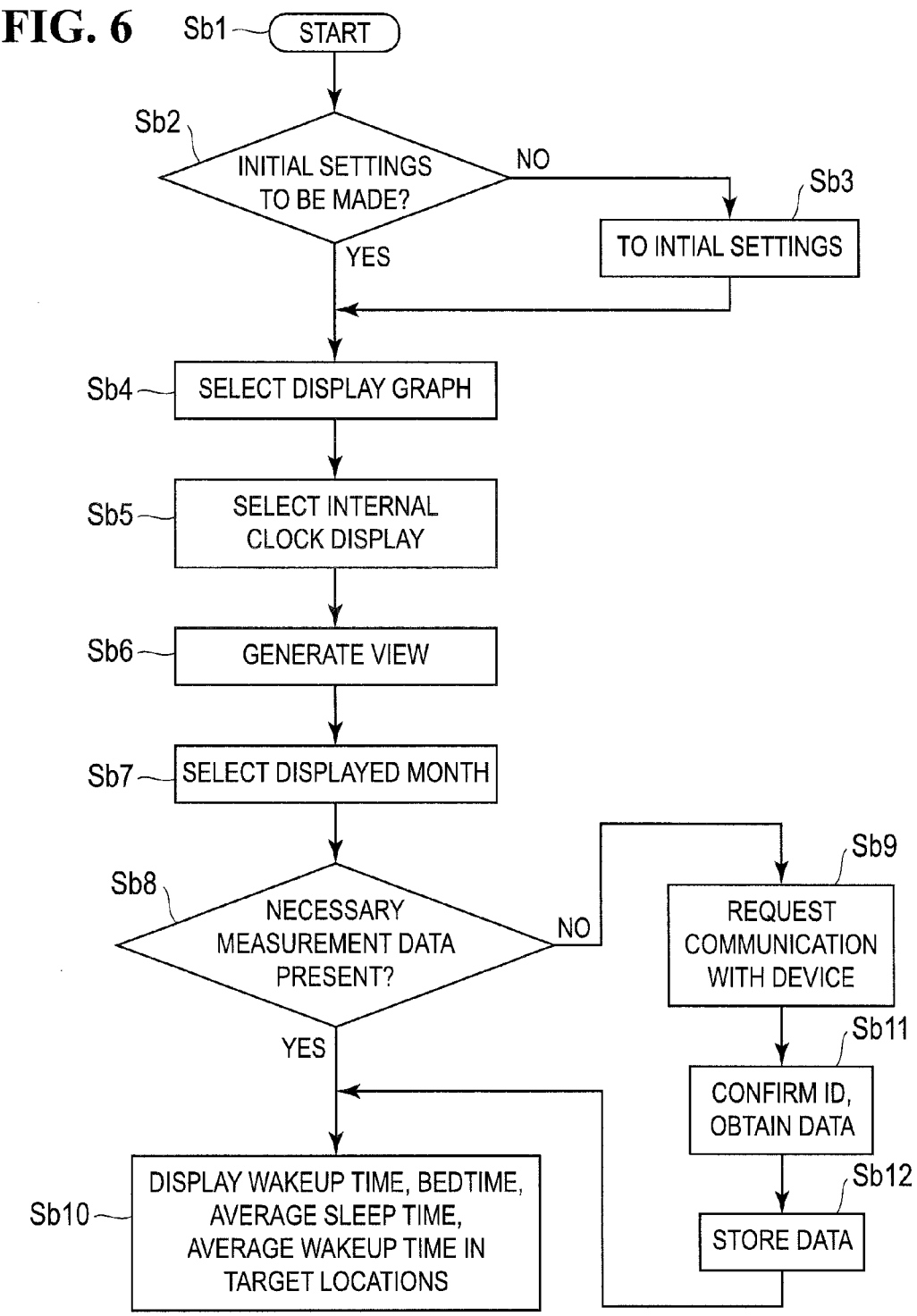
FIG. 6 is a flowchart illustrating basic operations of a sleep display program.
Figure 7:
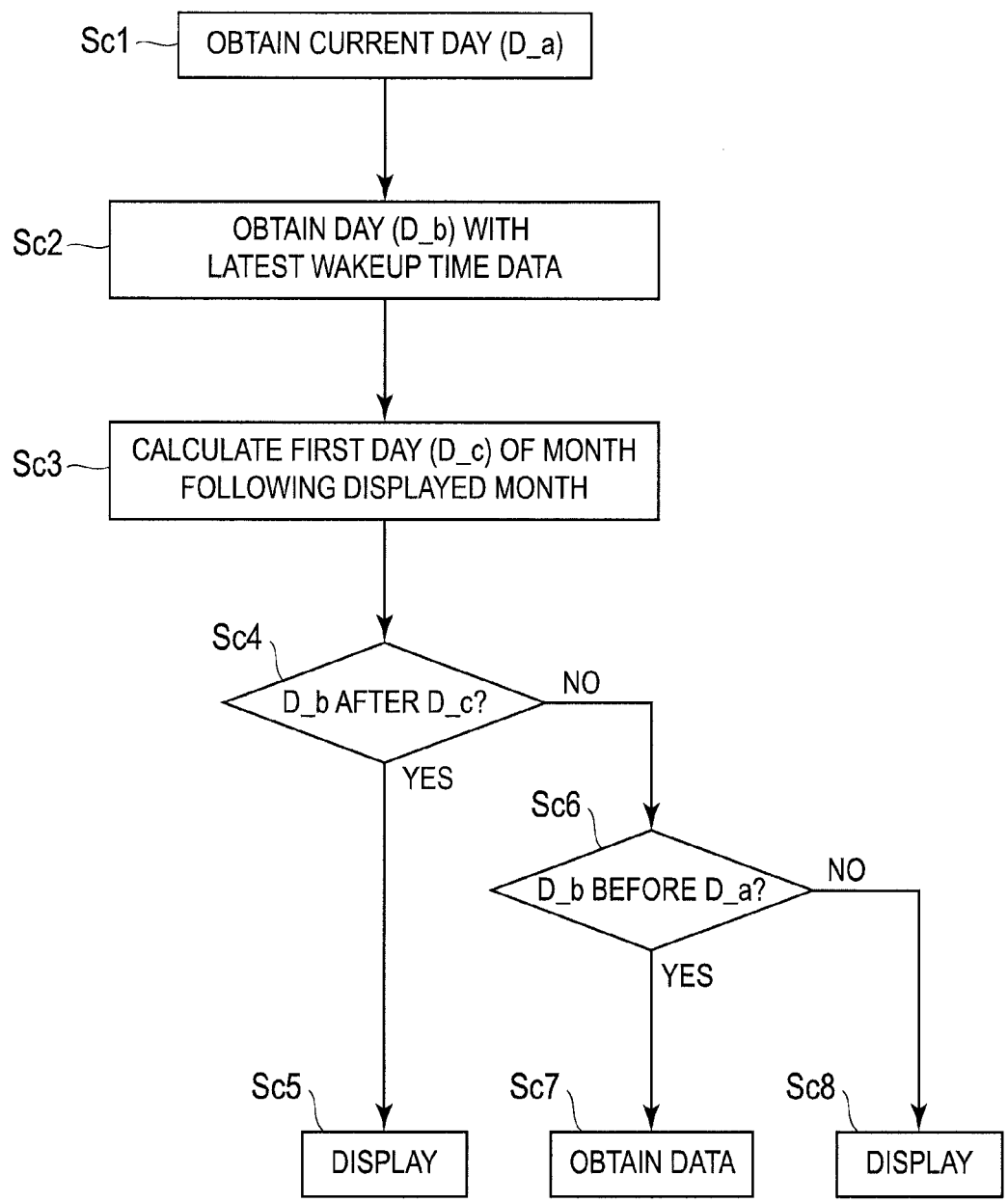
FIG. 7 is a flowchart illustrating basic operations of a sleep display program.

FIGS. 5 to 7 are examples of flowcharts illustrating basic operations of the sleep display program. FIG. 5 illustrates operations performed up until the sleep display device establishes communication with the sleep evaluation device and obtains a device ID; in step Sa1, a program of the sleep display device is launched, and in step Sat, necessary initial setting information is inputted. Then, in step Sa3, a communication request is issued to the sleep evaluation device. This step is repeated until a response to the communication request is received (step Sa4). When communication with the sleep evaluation device is established, the device ID of the sleep evaluation device is then obtained in step Sa5, the device ID is saved in step Sa6, and the process then ends (step Sa7). The device ID is a device-unique designation that identifies the sleep evaluation device.

FIG. 6 is a flowchart regarding control of the display screen displayed in the sleep display device. In step Sb1, the program is launched, and in step Sb2, it is determined whether there are initial settings to be made. In the case where the initial setting information is inputted or updated, the sleep display device transits to an initial setting input screen in step Sb3, and accepts the input of the necessary information. The process moves to step Sb4 in the case where the initial settings are not inputted or updated, and the sleep display device transits to a display screen selection mode. Then, in step Sb5, the sleep display device transits to an internal clock display selection mode, and generates a view in step Sb6. Then, in step Sb7, the sleep display device transits to a displayed month selection mode. Next, in step Sb8, it is determined whether or not the sleep state data from the sleep evaluation device has been updated. In the case where the data has been updated, in step Sb9, a communication request is issued to the sleep evaluation device, the device ID is obtained and stored (step Sb11), and the sleep state data is obtained (step Sb12). However, in the case where the sleep state data has not been updated, the 24-hour circular time display image that is divided into time periods indicating predetermined time spans is displayed in the display unit, and the data of past records is displayed in a target location of the display unit. When plotting data repeatedly in the same location, it is preferable to vary the brightness as described above.

FIG. 7 is a flowchart illustrating details of step Sb8 in FIG. 6, in which it is determined whether or not the data has been updated. Whether or not the data has been updated is determined by obtaining a current day (D_a) in step Sc1 and then obtaining a day (D_b) in which the most recent wakeup time ($T_W$) was recorded in step Sc2. Next, in step Sc3, the first day (D_c) of the month following the displayed month is calculated. Then, in step Sc4, the day (D_b) in which the most recent wakeup time was recorded obtained in step Sc2 is compared with the first day (D_c) of the month following the displayed month calculated in step Sc3, and in the case where the day in which the most recent wakeup time was recorded comes after the first day of the month following the displayed month, the data is displayed (Sc5). When such is not the case, however, in step Sc6, the day (D_b) in which the most recent wakeup time was recorded is compared with the current day (D_a), and in the case where the day (D_b) in which the most recent wakeup time was recorded comes before the current day (D_a), it can be determined that the data has been updated; thus in step Sc7, the updated data is obtained. When such is not the case, in step Sc8, the data that is currently held is displayed.

Usage Method

The user starts measurement by placing the sleep evaluation device 100 near his/her pillow. The next morning, the sleep state data is transferred to the mobile information terminal. By operating the mobile information terminal, the user confirms how much s/he slept the night before. The user inputs a "refreshed" star if s/he woke up feeling refreshed. The user also enters items of particular interest, such as events that happened that day, in a "memo" section. After one week, the user confirms the extent to which the bedtimes and wakeup times varied and how much s/he sleeps on average throughout the week. This prompt the user to improve his/her sleep rhythm. By also obtaining the number of times the snooze function was used and displaying that number along with the "refreshed level" in this one-week display, the user can understand the number of times s/he snoozed in relation to a high "refreshed level", which can serve as an indicator of how best to wake up.

Although the foregoing descriptions have assumed that the image displays are rendered by a program running on the terminal, an external server that processes the data of the sleep evaluation device may be provided, and the necessary display screen data may be rendered by executing the stated program in the external server and then downloaded to the terminal as image data instead.

Second Embodiment

In the case where the "terminal" in the first embodiment is a mobile information terminal such as a smartphone in particular, the terminal includes an accelerometer and a camera function, in addition to a CPU and a memory for controlling sensors and saving data obtained from those sensors, a communication interface for communicating with the exterior, and so on. Accordingly, the mobile information terminal that is to serve as the "sleep display device" can itself detect body movement and obtain the sleep state data. In other words, an embodiment can be considered in which the same mobile information terminal functions both as the sleep evaluation device and as the sleep display device. The mobile information terminal is configured as indicated by the block diagram illustrating a specific example of the hardware configuration of the sleep evaluation device 100 shown in FIG. 4A in order to realize the functionality of the sleep evaluation device in such a case. Note that the sleep evaluation device 100 is used while the user is asleep and the sleep display device is used while the user is awake, and are therefore originally used independently from each other; accordingly, the devices may have the same physical configuration, such as the CPU of the control unit and so on, but may be configured as different programs that operate independently from each other.

The invention claimed is:

1. A non-transitory computer-readable medium comprising a sleep display program for displaying, in a display unit, sleep state data of a user that has been measured and recorded by a sleep evaluation device, the data including at least a wakeup time $T_W$ and a bedtime $T_Z$, and the program comprising:

a step of obtaining the data from the sleep evaluation device;

a step of displaying, in the display unit, an image comprising a 24-hour circular time display image of a 24-hour time span that is divided into a plurality of time sections, each section of the plurality of time sections indicating a time span of a predetermined number of minutes, said each section being configured to record the wakeup time in a first color and the bedtime in a second color wherein:

the brightness of one color of the first color or the second color is at a first brightness level for a first instance of recording at a location on the plurality of time sections of the 24-hour circular time display image, the brightness of the one color is at a second brightness level, which is greater than the first brightness level, for a second instance of recording, which is subsequent to the first instance of recording, at the location on the plurality of time sections of the 24-hour circular time display image, which is a same location as the location where the first instance is recorded, and the brightness of the one color is at a third brightness level, which is greater than the second brightness level, for a third instance of recording, which is subsequent to the second instance of recording, at the location on the plurality of time sections of the 24-hour circular time display image, which is a same location as the location where the second instance is recorded; and a step of plotting, on the time periods in the 24-hour circular time display image of the 24-hour time span, records of the wakeup times $T_W$ and the bedtimes $T_Z$ for a plurality of days included in the data such that the user can visualize variations in the wakeup times $T_W$ and the bedtimes $T_Z$ for the plurality of days, wherein the records are displayed visually in the 24-hour circular time display image of the 24-hour time span in association with an area, number, or color of a graphic or a combination thereof.

2. The non-transitory computer-readable medium according to claim 1, the program further comprising:

a step of inputting a subjective impression of the quality of the user's sleep after waking as a graded sleep evaluation index; and a step of visually displaying a result of the input in association with an area, number, or color of a graphic or a combination thereof.

3. The non-transitory computer-readable medium according to claim 1, the program further comprising:

a step of visually displaying a cumulative value of the sleep evaluation index from a point in the past to the present.

4. The non-transitory computer-readable medium according to claim 1, wherein the data includes a planned wakeup time $T_S$, the program further comprising:

a step of displaying, in the 24-hour circular time display image of the 24-hour time span, a recommended bedtime period $T_{ZZ}$ set to a certain amount of time after a most recent planned wakeup time $T_S$.

5. The non-transitory computer-readable medium according to claim 4,
wherein an end time of the recommended bedtime period does not exceed a pre-set time.

6. The non-transitory computer-readable medium according to claim 1, the program further comprising:
a step of displaying, in the 24-hour circular time display image of the 24-hour time span, a recommended wakeup time period $T_{ZW}$ calculated based on one of an average of planned wakeup times set in the past and the latest planned wakeup time that is currently set.

7. A sleep display device in which is installed the sleep display program according to claim 1.

8. A sleep display device for displaying, in a display unit, sleep state data of a user that has been measured and recorded by a sleep evaluation device, the data including at least a wakeup time $T_W$ and a bedtime $T_Z$, and the sleep display device comprising:
a means for obtaining the data from the sleep evaluation device;
a means for displaying, in the display unit, an image comprising a 24-hour circular time display image of a 24-hour time span that is divided into a plurality of time sections, each section of the plurality of time sections indicating a time span of a predetermined number of minutes, said each section being configured to record the wakeup time in a first color and the bedtime in a second color wherein:
the brightness of one color of the first color or the second color is at a first brightness level for a first instance of recording at a location on the plurality of time sections of the 24-hour circular time display image,
the brightness of the one color is at a second brightness level, which is greater than the first brightness level, for a second instance of recording, which is subsequent to the first instance of recording, at the location on the plurality of time sections of the 24-hour circular time display image, which is a same location as the location where the first instance is recorded, and
the brightness of the one color is at a third brightness level, which is greater than the second brightness level, for a third instance of recording, which is subsequent to the second instance of recording, at the location on the plurality of time sections of the 24-hour circular time display image, which is a same location as the location where the second instance is recorded; and
a means for plotting, on the time periods in the 24-hour circular time display image of the 24-hour time span records of the wakeup times $T_W$ and the bedtimes $T_Z$ for a plurality of days included in the data such that the user can visualize variations in the wakeup times $T_W$ and the bedtimes $T_Z$ for the plurality of days,
wherein the records are displayed visually in the 24-hour circular time display image of the 24-hour time span in association with an area, number, or color of a graphic or a combination thereof.

9. A sleep display method for displaying, in a display unit, sleep state data of a user that has been measured and recorded by a sleep evaluation device, the data including at least a wakeup time $T_W$ and a bedtime $T_Z$, and the method comprising:
a step of obtaining the data from the sleep evaluation device;
a step of displaying, in the display unit, an image comprising a 24-hour circular time display image of a 24-hour time span that is divided into a plurality of time sections, each section of the plurality of time sections indicating a time span of a predetermined number of minutes, said each section being configured to record the wakeup time in a first color and the bedtime in a second color wherein:
the brightness of one color of the first color or the second color is at a first brightness level for a first instance of recording at a location on the plurality of time sections of the 24-hour circular time display image,
the brightness of the one color is at a second brightness level, which is greater than the first brightness level, for a second instance of recording, which is subsequent to the first instance of recording, at the location on the plurality of time sections of the 24-hour circular time display image, which is a same location as the location where the first instance is recorded, and
the brightness of the one color is at a third brightness level, which is greater than the second brightness level, for a third instance of recording, which is subsequent to the second instance of recording, at the location on the plurality of time sections of the 24-hour circular time display image, which is a same location as the location where the second instance is recorded; and
a step of plotting, on the time periods in the 24-hour circular time display image of the 24-hour time span, records of the wakeup times $T_W$ and the bedtimes $T_Z$ for a plurality of days included in the data such that the user can visualize variations in the wakeup times $T_W$ and the bedtimes $T_Z$ for the plurality of days,
wherein the records are displayed visually in the 24-hour circular time display image of the 24-hour time span in association with an area, number, or color of a graphic or a combination thereof.

* * * * *